United States Patent [19]
Friedman

[11] Patent Number: 4,643,195

[45] Date of Patent: Feb. 17, 1987

[54] ATTACHMENT FOR DETERMINING HUMAN REFLEX REACTIONS AND METHOD FOR DETERMINING SAME

[76] Inventor: Robert H. Friedman, 2828 Stonington Pl., St. Louis, Mo. 63131

[21] Appl. No.: 648,480

[22] Filed: Sep. 10, 1984

[51] Int. Cl.[4] .............................................. A61B 5/16
[52] U.S. Cl. ................................................. 128/740
[58] Field of Search ....................... 128/740, 739, 744; 145/29 B; 74/551.9; D8/DIG. 6, DIG. 7, DIG. 8

[56] References Cited

U.S. PATENT DOCUMENTS

| | | | |
|---|---|---|---|
| 2,315,160 | 3/1943 | Newstedt | 128/740 |
| 2,666,340 | 1/1954 | Hunt | 74/551.9 |
| 2,908,268 | 10/1959 | Guest | 128/740 |
| 3,344,781 | 10/1967 | Allen | 128/739 |
| 3,515,125 | 6/1970 | Ruskin | 128/740 |

Primary Examiner—William E. Kamm
Attorney, Agent, or Firm—Kalish & Gilster

[57] ABSTRACT

A reflex hammer having a tubular body dimensioned for readily attachable frictional engagement upon the elongated body of a preselected medical treatment, the hammer being fabricated of flexible, resilient material and incorporating a head projecting beyond the periphery of the wall of the hammer.

13 Claims, 4 Drawing Figures

ATTACHMENT FOR DETERMINING HUMAN REFLEX REACTIONS AND METHOD FOR DETERMINING SAME

BACKGROUND AND SUMMARY OF THE INVENTION

This invention relates in general to neurological instruments and, more particularly, to a reflex hammer for attachment upon a handle-forming instrument.

Heretofore, there has been an established recognition of the desirability of incorporating a reflex or percussion hammer for neurological diagnostic purposes with a coordinating instrumentality; thereby forming a composite device which obviates the need for a physician to have a separate independent hammer. In comprehensively physically examining a patient, a physician should check the deep nerve reflexes as by striking above the patella on the knee to cause the knee to jerk in order to determine the character of the nerve circuitry. With relative frequency, a physician may find when making such an examination away from his office or a hospital that a reflex or percussion hammer has been misplaced or forgotten and thus the examination is perforce not completed.

In order to obviate such a contingency, there have been various efforts made heretofore so as to integrate a reflex hammer within a composite instrument. One such prior art structure is revealed in the Golub et al, U.S. Pat. No. 2,532,093. This patent discloses an instrument incorporating a handle which at one end has the conventional head crosswise permanently fixed thereon and with said handle at its other end being engageable to a cylindrical casing for housing other neurological diagnostic implements such as a brush and a needle. The Guest U.S. Pat. No. 2,908,268, shows another effort at providing a composite diagnostic instrument which incorporates a handle-forming casing for a tuning fork and with the handle or extension of the latter being suitably engageable to a socket member which mounts a triangular rubber impact or hammer head. The Leopoldi U.S. Pat. No. 3,185,146, reveals another attempt at providing a diagnostic instrument of which the reflex hammer constitutes but a portion. In this particular embodiment, the hammer end, having two ends, is pivotally mounted upon one end of a telescoping handle structure and thus being permanently integrated therewith; said handle structure internally providing a chamber for receiving associated diagnostic implements such as a brush has a pin.

It will thus be seen that the prior art discloses only fixedly integrated structures, but, nonetheless, demonstrate the recognized need for diagnosticians to be provided with a reflex hammer which is not of independent construction but is integrated within a composite instrumentality.

The present invention contemplates the provision of a reflex hammer component which is of independent construction but which is readily attachable, or otherwise detachably engageable, upon another instrument which may be for neurological examination, but not necessarily, and alone as it is of such nature as to provide a handle. Thus, the present invention involves a hammer of sleeve-form which simply frictionally engages the body of another instrument.

Therefore, it is an object of the present invention to provide a reflex hammer attachment for neurological diagnostic purposes which is readily detachably engageable upon another instrument or supporting device.

It is another object of the present invention to provide a reflex hammer attachment of the type stated which is constructed of suitable flexible and resilient material so as to easily accommodate the supporting instrument.

It is still another object of the present invention to provide a reflex hammer attachment of the character stated which accordingly may be detachably mounted upon any suitable instrument or device and not necessarily one which is useful for neurological diagnosis.

It is a still further object of the present invention to provide a reflex hammer of the type stated which is most economically manufactured so that loss or misplacement of the same does not entail a substantial economic loss as would be with currently available reflex hammer; which is easily mounted upon the selected handle-forming support and is secured thereon for assuring of reliable usage; and which is constructed of durable material but which is of relatively light weight so as to be a negligible weight factor in a physician's bag.

It is a still further object of the present invention to provide a method for using a reflex hammer attachment of the character above stated for determining human reflex reactions.

DESCRIPTION OF THE PREFERRED EMBODIMENT

Figure 2:
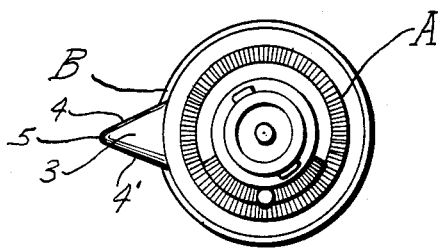
FIG. 2 is a top plan view.
Figure 1:
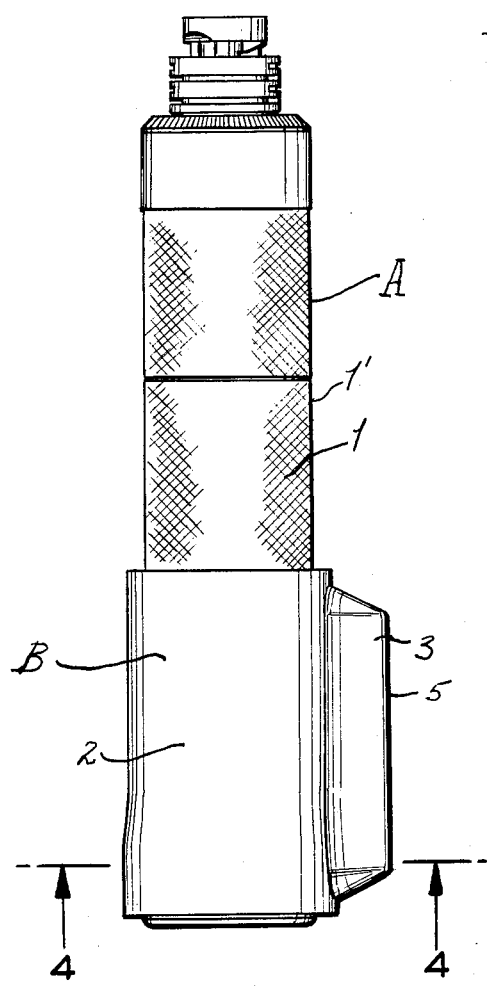
FIG. 1 is a side elevational view of an instrument having mounted thereon a reflex hammer constructed in accordance with and embodying the present invention.
Figure 3:
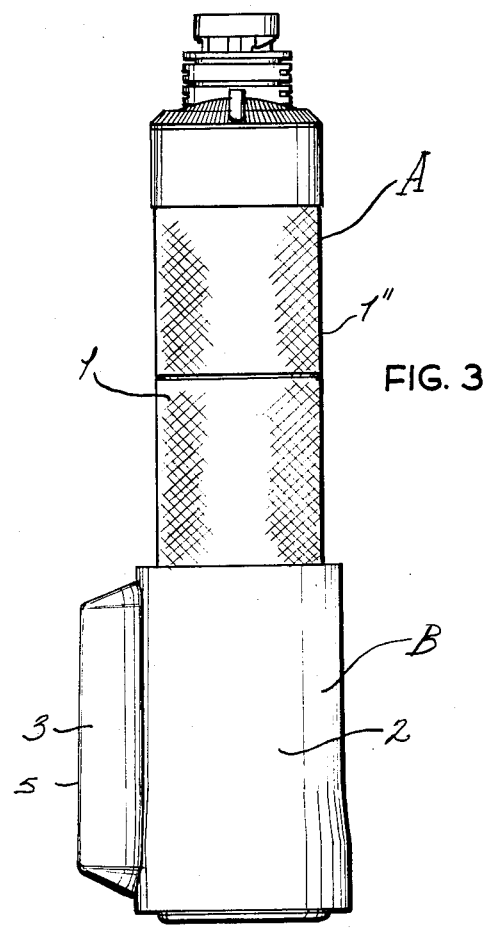
FIG. 3 is an elevational view of the instrument illustrated in FIG. 1, but shown at an angle of 180° therefrom.
Figure 4:
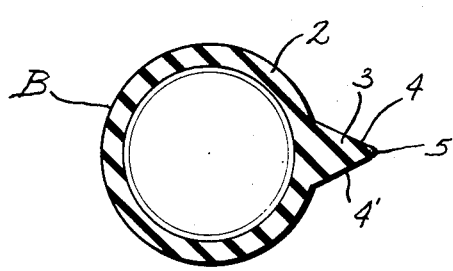
FIG. 4 is a horizontal transverse sectional view taken on the line 4—4 of FIG. 1.

Referring now by reference characters to the drawing which illustrates the preferred embodiment of the present invention, A generally designates a medical instrument such as for diagnostic purposes which comprises an elongated rigid body 1 embodying a handle-defining portion 1' and which carries at one end portion thereof a particular tool or working element, as at a. The exact nature of instrument A is immaterial but for purposes of illustration, comprehends an ophthalmoscope as utilized in neurological examination. Thus, it is to be understood that instrument A is not a part of the present invention, but simply exemplifies a commonly used medical instrument of elongate character and having a rigid body of such overall, length adequate for accommodating the present invention, as set forth below, while not interfering with the operation or effective utilization of the tool or work element a; it being understood that such body 1 may be solid or hollow in accordance with the particular purpose of such instrument.

Provided for optional, frictional engagement upon body 1 of instrument A is a reflex or percussion hammer B which constitutes a tube or sleeve having a preferably circular wall 2 and being open from end to end throughout its length. Said hammer 2 is fabricated of durable, flexible and resilient material such as preferably natural or synthetic rubber or a suitable plastic and having an inside diameter or cross section substantially complementary to the outside diameter or cross-section of body 1 of instrument A so that hammer B may snuggly receive the normally inoperative end of body 1. It will thus be seen that the aforesaid relationship must be such as to assure that hammer B will be tightly engaged about body 1 so as to avoid any undesired or accidental axial rotation thereabout, much less inadvertent displacement from instrument A. It is to be recognized that the handle-defining portion 1' is of such overall length that a substantial portion 1" of the same remains uncovered when hammer B is engaged upon said rigid body 1 to be available for gripping for appropriate manipulation of the hammer attachment as well as the particular tool or working element a. Integrally formed with hammer wall 2 is a lengthwise extending continuous head-forming portion or head 3 which may be substantially coextensive wwith said wall 2. Said head 3 is of generally triangular character and cross section having outwardly converging sides 4, 4' which terminate in a relatively narrow striking edge or ridge forming portion 5. Head 3 may be of any other suitable configuration for contacting the patient's body such as at the knee or elbow region for provoking the particular response. The particular edge-developing head 3 is thus shown for exemplary purposes, as the same does lend itself for facilitating production, as well as being efficient for the intended purposes. Thus, it would be within the scope of one having skill in the art to cause such head to be of an arcuated nature as shown in the Guest patent, above noted, or to be of the more familiar generally rounded configuration.

It is to be understood that hammer B may be, of course, produced to the size desired for accommodating instruments of different outer diameter or cross section and the thickness of wall 2 may, of course, be varied so as to provide the requisite durability, as well as reliability in operation.

Thus, with the present invention, a physician may select any particular instrument he wishes to mount the hammer B upon, but necessarily will utilize a hammer B of commensurate inside diameter or cross section. Instrument A thus by reason of the detachable engagement of hammer B thereon develops a composite character with one end portion of body 1 supporting hammer B and the remaining portion serving as a handle for such hammer. Accordingly, hammer B is actually an accessory for any suitable instrument and yet in and of itself functions as efficiently as the customary self-contained, independent, currently-used reflex hammers. Head 3 is of adequate thickness and hardness so as to impart the requisite blow to the body zone for assuring accuracy of response.

Therefore, it is quite apparent that hammer B may be most economically manufactured so that the displacement of the same will not necessitate a substantial expense for replacement as would be the base with currently used reflex hammer and manifestly the utilization of hammer B relieves the concern as to the ready availability of another instrument.

It is, of course, understood that head 3, if desired, could be constructed dependently of wall 2 and being formed of any preselected suitable material and fixed upon said tubular wall 2 by requisite means. However, it is quite obvious that the embodiment above discussed and shown in the drawings is preferable in that it is manifestly cheaper to fabricate and will be of relative strength so as to assure of maximum durability.

What is claimed is:

1. The combination with a portable, manually manipulative medical instrument having an elongated rigid body incorporating a handle, said instrument having a tool or a working element provided at one end thereof and being free in the end portion remote from said tool, of a reflex hammer comprising a body of tubular form being open at the opposite ends thereof, the inside cross-section of said tubular body being substantially complementary to the outside cross-section of the handle of said instrument to effect a detachable, snug, yet operationally reliable disposition thereon, said tubular body being of less axial length than said instrument handle, said tubular body being frictionally fitted over a portion of the tool-remote end portion of said handle whereby a portion of said handle between said tubular body and the tool is not covered by said tubular body, said tubular body being provided on the outer surface thereof with a continuous ridig-forming projection extending outwardly therefrom and defining an impact surface, said tubular body being of such overall length that the uncovered portion of said handle is of adequate extent for gripping by the user for applying the impact surface of the hammer for medical diagnostic purposes as well as for appropriate manipulation of the tool.

2. The combination as defined in claim 1 and further characterized by said hammer tubular body being fabricated of flexible, resilient material from the class consisting of natural rubber, synthetic rubber, and plastic.

3. The combination as set forth in claim 1 wherein said hammer tubular body is fabricated of resilient flexible material.

4. The combination as set forth in claim 1 wherein said ridge-forming projection is axially parallel to said tubular body.

5. The combination as set forth in claim 1 wherein said tubular body is of circular cross-section and with the inside diameter thereof being complementary to the outside diameter of the instrument handle.

6. The combination as set forth in claim 1 wherein the ridge-forming projection is of elongated, rectilinear configuration.

7. An accessory for a portable, manually manipulative medical instrument having an elongated rigid handle portion comprising a reflex hammer having a body of tubular form, said body being open at the opposite ends thereof, said body being provided on the outer portion thereof with a continuous ridge-forming projection extending laterally outwardly therefrom and defining an impact surface.

8. An accessory as defined in claim 7 wherein the ridge-forming projection incorporates side portions which coverage outwardly from said tubular body toward said projection.

9. An accessory as set forth in claim 7 wherein said hammer tubular is fabricated of resilient flexible material.

10. An accessory as set forth in claim 7 wherein set ridge-forming projection is axially parallel to said tubular body.

11. An accessory as set forth in claim 7 wherein said tubular body is of circular cross-section and with the inside diameter thereof being complementary to the outside diameter of the instrument handle.

12. An accessory as set forth in claim 7 wherein the ridge-forming projection is of elongated, rectilinear configuration.

13. A method for determining human reflex reactions comprising providing a portable, manually manipulative medical instrument having an elongated rigid body incorporating a handle, said instrument having a tool or working element provided at one end thereof and being free in the end portion remote from said tool, mounting a reflex hammer upon the portion of said instrument handle adjacent the free end thereof, said reflex hammer having a tubular body open at the opposite ends thereof, the inside cross-section of said tubular body being substantially complementary to the outside cross-section of the handle of said instrument to effect a snug, frictional, operationally reliable disposition thereupon, said tubular body being of less axial length than said instrument handle thereby causing a portion of said hammer to be uncovered when said hammer is engaged thereon to permit manual gripping of said uncovered portion for utilization of the hammer, a continuous ridge-forming projection provided on the outer portion of said tubular body and extending laterally outwardly therefrom for defining an impact surface, and then striking the physiological portion to be tested by said impact surface through suitable manipulation of the uncovered instrument handle in order to observe the reflexive action of the human joint stricken.

* * * * *